(12) United States Patent
Zinchenko et al.

(10) Patent No.: US 8,298,393 B2
(45) Date of Patent: Oct. 30, 2012

(54) METHOD OF ELECTROPHORETIC ANALYSIS OF MULTICOMPONENT SOLUTIONS AND DEVICE FOR PERFORMING THE SAME

(75) Inventors: Mikhail Ivanovich Zinchenko, St. Petersburg (RU); Yaroslav Sergeevich Kamentsev, St. Petersburg (RU); Mikhail Yaroslavovich Kamentsev, St. Petersburg (RU); Slyadnev Nikolaevich Maksim, St. Petersburg (RU); Alexander Anatolevich Stroganov, St. Petersburg (RU)

(73) Assignee: Lumex Instruments Limited, Nicosia (CY)

( * ) Notice: Subject to any disclaimer, the term of this patent is extended or adjusted under 35 U.S.C. 154(b) by 687 days.

(21) Appl. No.: 12/280,386

(22) PCT Filed: Feb. 5, 2007

(86) PCT No.: PCT/RU2007/000065
§ 371 (c)(1),
(2), (4) Date: Aug. 22, 2008

(87) PCT Pub. No.: WO2007/097660
PCT Pub. Date: Aug. 30, 2007

(65) Prior Publication Data
US 2009/0038943 A1 Feb. 12, 2009

(30) Foreign Application Priority Data
Feb. 26, 2006 (RU) ................................ 2006106665

(51) Int. Cl.
*G01N 27/453* (2006.01)
(52) U.S. Cl. ........................................ 204/604; 204/454

(58) Field of Classification Search .................. 204/453, 204/454, 604
See application file for complete search history.

(56) References Cited

U.S. PATENT DOCUMENTS 5,441,613 A   8/1995   McCormick et al.

FOREIGN PATENT DOCUMENTS

| CA | 2484804 A1 | 12/2003 |
|----|------------|---------|
| RU | 1827636 A1 | 7/1993  |
| SU | 500502     | 1/1976  |
| SU | 1087864 A1 | 4/1984  |

(Continued)

OTHER PUBLICATIONS

Kamentsev et al. "Measurement of flow potential for on-line monitoring of capillary surface quality during capillary electrophoresis analysis" Abstracts of the 230th ACS National Meeting, Washington, DC, Paper No. ANYL 239, publicly available on Jul. 4, 2005.*

(Continued)

*Primary Examiner* — J. Christopher Ball
(74) *Attorney, Agent, or Firm* — Christopher L. Parmelee; Walker & Jocke (57) ABSTRACT

A device for electrophoretic analysis of multicomponent solutions comprises a capillary and vials for electrolyte and sample solutions. The device comprises streaming potential measurement means implemented to measure a potential difference between capillary ends and to form an electric connections with said capillary ends during capillary rinsing in such a way that said streaming potential measurement means and electrolyte inside capillary and vials form a closed measurement electric circuit. A means for generation of electrolyte flow is implemented so as to build up and maintain a preset differential pressure between capillary ends and wherein that streaming potential measurement means comprises means to disconnect said measurement electric circuit during electrophoretic analysis.

7 Claims, 6 Drawing Sheets

FOREIGN PATENT DOCUMENTS

| | | | |
|---|---|---|---|
| SU | 1567957 | A1 | 5/1990 |
| SU | 1597628 | A1 | 10/1990 |

OTHER PUBLICATIONS

Webpage presentation by OKUN, "Capillary Electrophoresis System CAPEL-105M", accessed from http://www.rmi.cz/content/stat.php?id=343&modul=produkty_soubory on Mar. 8, 2011.*

Webpage: "Capillary Electrophoresis System CAPEL-105M", accessed from the following URL on Nov. 3, 2011: http://www.plasmatronics.com.br/Capel.pdf.*

Capillary Electrophoresis System. Bases of the method. Equipment. Examples of capillary electrophoresis system use "Kagel—103,—104,—105". SPb, "Petropolis" Publishing House 2001.

* cited by examiner

METHOD OF ELECTROPHORETIC ANALYSIS OF MULTICOMPONENT SOLUTIONS AND DEVICE FOR PERFORMING THE SAME

The present invention relates to analytical chemistry, more particularly, to methods of electrophoretic analysis, and can be utilized to analysis of multicomponent solutions.

Several approaches of electorphoretic analysis of multicomponent solutions are known (1, 2, 3), based on separation of mixture components in a quartz capillary by applying high voltage electric field.

In capillary electrophoretic analysis, analysed sample is injected into a capillary, that was preliminarily washed and filled with electrolyte solution (known as a buffer solution). After high voltage is applied across both capillary ends, mixture components begin to migrate with different velocity. When a migrating analyte reaches a detector located at a specified distance from capillary inlet, analytical signals proportional to analytes quantity as well as retention times of analytes are measured. Retention time is calculated as an interval between an onset of electrophoretic separation and time point when a component is being detected.

Generally, in case of photometric, fluorimetric, or other optical detector a section of the capillary serves as a detector zone. In case of mass-spectrometric detector, a detector zone is located at the capillary outlet. Detector response recorded when a single analyte pass through the detector zone is known as electrophoretic peak. Detector response recorded as a function of time is known as an electropherogram, that can be used for qualitative identification and quantitative determination of analytes that correspond to different peaks.

Identification of different sample components is achieved by juxtaposition of their retention times with retention times of analytes in calibration solution. Quantitative determination of sample analytes is achieved by comparison of analytical signals detected during electrophoretic separations of sample solution with that of calibration (standard) solution.

US Patent (5) describes a method and device for a real-time detection and control of electroosmotic flow.

In process of electrophoretic separation of solutions the charged particle migration rate in capillary is equal to particle electromigration rate subject to features of particle itself (its charge, mass and conformation) added algebraically to electroosmotic flow (EOF) rate depending on capillary features. Given the specified composition and concentration of buffer electrolyte EOF rate is determined by equation:

$$A_{eof} = \zeta \frac{\varepsilon E}{4\pi \eta}, \quad (1)$$

where $A_{eof}$—EOF rate, $\zeta$—electrokinetic surface potential, $\varepsilon$—dielectric constant of solution, E—electric-field intensity, $\eta$—solution viscosity of buffer electrolyte. Equation shows that EOF rate, other things being equal, is proportional to electrokinetic surface potential magnitude ($\zeta$-potential), determined by composition and structure of double electric layer formed between inner capillary surface and electrolyte. Equilibrium value of $\zeta$-potential for clean capillary surface under the given conditions is the maximal value, in which case EOF rate is maximal, and component retention time is minimal. If the procedure of capillary washing is not used after analysis, the component retention time in successive sample injections increases. It testifies decreasing of $\zeta$-potential magnitude because of capillary inner surface contamination by the absorbed admixtures, changing double electric layer composition. In case of substantial change of components retention time owing to capillary contamination the errors of identification of multicomponent mixture components may arise.

The method closest to proposed invention is described in ref. (4), it comprises of calibration and analytic measurements, including capillary washing by electrolyte solution, injection of calibration mixture into capillary filled with electrolyte in process of calibration measurements and injection of sample solution in process of analytic measurements, electrophoretic separation of components of injected solutions in capillary under the voltage applied between the capillary ends, detection and measurement of retention time of injected solution components, as well as identification of sample components subject to retention times.

Capillary washing after analysis provides removal of sample components from a capillary, which migrated towards electroosmotic flow, as well as provides cleaning of capillary wall from adsorbed admixtures. For most efficient capillary cleaning, different washing solutions are selected subject to its operation conditions. Particularly, new capillary or capillary not used for a long time are washed successively by acid solution, water, alkali solution, by water again and then conditioned by rinsing with electrolytic solution. Required cleaning efficiency of capillary walls from absorbed admixtures is reached by empirical choice of compositions of washing solution and washing time for each of them. Cleaning efficiency is determined after analysis based on the retention time reproducibility for analytes.

To implement the mentioned method an apparatus is described (4), comprising of a capillary, vials for electrolyte and samples, means for capillary and vials installation providing possibility of placing capillary ends to the mentioned vials, means for generation electrolyte flow through a capillary, means for applying voltage between capillary ends, detector connected with a capillary, as well as control and signal processing systems.

Essential disadvantages of the mentioned method and apparatus are the following facts: cleaning efficiency may be revealed only after making the next analysis, as well as the fact that correctness of empiric choice of capillary washing conditions depends on operator's qualification, i.e. it is not objectivistic. Insufficient or indefinite capillary walls cleaning efficiency causes insufficient reproducibility of retention times of analytes, which is revealed only after making analysis. The reason of irreproducibility is uncontrolled scatter of EOF rate $A_{eof}$ for different analyses, which may change as a result of admixtures sorption from sample solution to capillary surface, these admixtures disturbing electric double layer structure. That makes sample component identification difficult and increases error of mixing ratio quantitative estimation, and in some cases requires repeated sample analysis.

To compensate uncontrolled rate changes of electroosmotic flow in prototype (4), electroosmotic flow markers (hereinafter referred to as EOF markers) are used, i.e. components with zero or low electrophoretic mobility (electromigration rate) specially added into sample in this buffer, retention time of which enables to estimate electroosmotic flow rate and correct retention times of analytes, that is to make computed corrections. Use of the said EOF markers substantially increases analysis cost. Besides such a method is not versatile, because different types of buffer solution require different EOF markers. Another disadvantage of EOF markers method is the fact that it is inapplicable for negative electroosmotic flow rate, as in this case EOF markers do not reach detection area at all.

It is an objective of the present invention to increase reproducibility of electrophoretic analysis of multicomponent solutions, and to increase sample throughput for electrophoretic analysis of large number of samples.

To achieve this objective we propose to use the method of electrophoretic analysis of multicomponent solutions, comprising of calibration and analytic measurements, namely capillary washing by electrolytic solution, injection of calibration mixture into capillary filled with electrolyte in process of calibration measurements and injection of sample solution in process of analytic measurements, electrophoretic separation of injected solutions components in capillary effected by voltage applied between the capillary ends, detection and measurement of retention times of injected solution components, identification of sample components subject to retention times; wherein during the process of capillary washing by electrolytic solution the streaming potential magnitude is measured by measuring a potential difference between capillary ends at definite pressure difference between said capillary ends.

To implement the method of electrophoretic analysis of multicomponent solutions the device is invented, comprising of a capillary, vials for electrolyte and samples, means for installation of capillary and vials made for immersing capillary ends to the said vials, means for creation of electrolyte flow through the capillary, means for applying voltage between capillary ends, detector connected with capillary, as well as control and signal processing systems; wherein the device contains the means for streaming potential measurement implemented to measure potential difference between capillary ends during application of a definite pressure differences between said capillary ends, providing electric connection with capillary ends at washing so that said devices for streaming potential measurement and electrolyte, being in vials and in capillary, together form the closed electric measurement circuit.

The essence of the present invention is a measurement of streaming potential in process of capillary washing with electrolyte solution during capillary preparation to analysis.

The method of present invention is based on unique correspondence between streaming potential magnitude and electroosmotic flow rate value $A_{eof}$.

In fact, streaming potential $U_s$, measured during capillary washing with electrolyte solution by means for measuring potential difference between capillary ends at definite pressure difference P between the said capillary ends, as well as electroosmotic flow rate $A_{eof}$, is proportionate to electrokinetic surface potential ($\zeta$—potential):

$$U_s = \zeta \frac{\varepsilon P}{4\pi\eta}, \quad (2).$$

The invention will be better understood with reference to the detailed description and the accompanying drawings, in which.

To prepare a capillary for electrophoretic separation it is rinsed with washing solutions, selected according to type of substances absorbed earlier, as well as the type of buffer electrolyte used in previous analyses. The last obligatory washing stage is capillary conditioning, i.e. rinsing with the same buffer electrolyte, which will be used in the next analysis. At the final washing stage in process of capillary conditioning streaming potential magnitude $U_s$ is determined.

For a clean capillary let's designate $U_s$ value, obtained before measurement of calibration of solution, by $U_{eq}$.

Capillary washing before analytic measurements is made until $U_s$ reaches the preset threshold $U_{s0}$.

Figure 1:
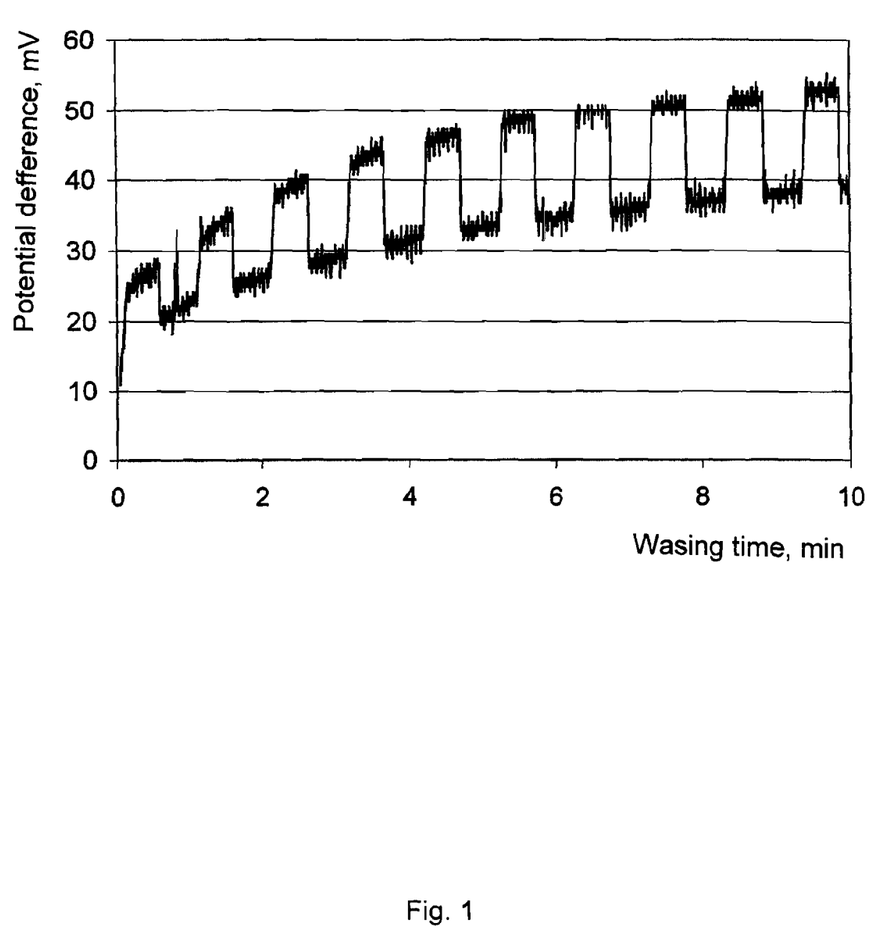
FIG. 1 shows potential difference between capillary ends as a function of time in successive washings of strongly contaminated capillary.

In process of washing, streaming potential magnitude approaches a certain magnitude, corresponding to equilibrium value of $\zeta$-potential. FIG. 1 shows typical streaming potential change in successive washings of strongly contaminated capillary. It is obvious, that during successive washings streaming potential increases successively, approaching equilibrium value.

The invention provides at least two approaches of achieving the objective of increasing reproducibility of electrophoretic analysis of multicomponent solutions by determination of streaming potential.

In the first case, capillary washing with electrolyte solution is performed until a limiting magnitude of streaming potential equal to value obtained before making electrophoretic separation of calibration (graduation) solution is achieved, then the scattering of electroosmotic flow rates and consequently retention times of sample components are reduced to a negligible level.

In the second case capillary washing is continued until a streaming potential magnitude somewhat less than limiting one is achieved, and for identification of components corrections are made, determined according to a ratio between the limiting magnitude of streaming potential and magnitude actually obtained in process of washing.

Figure 2:
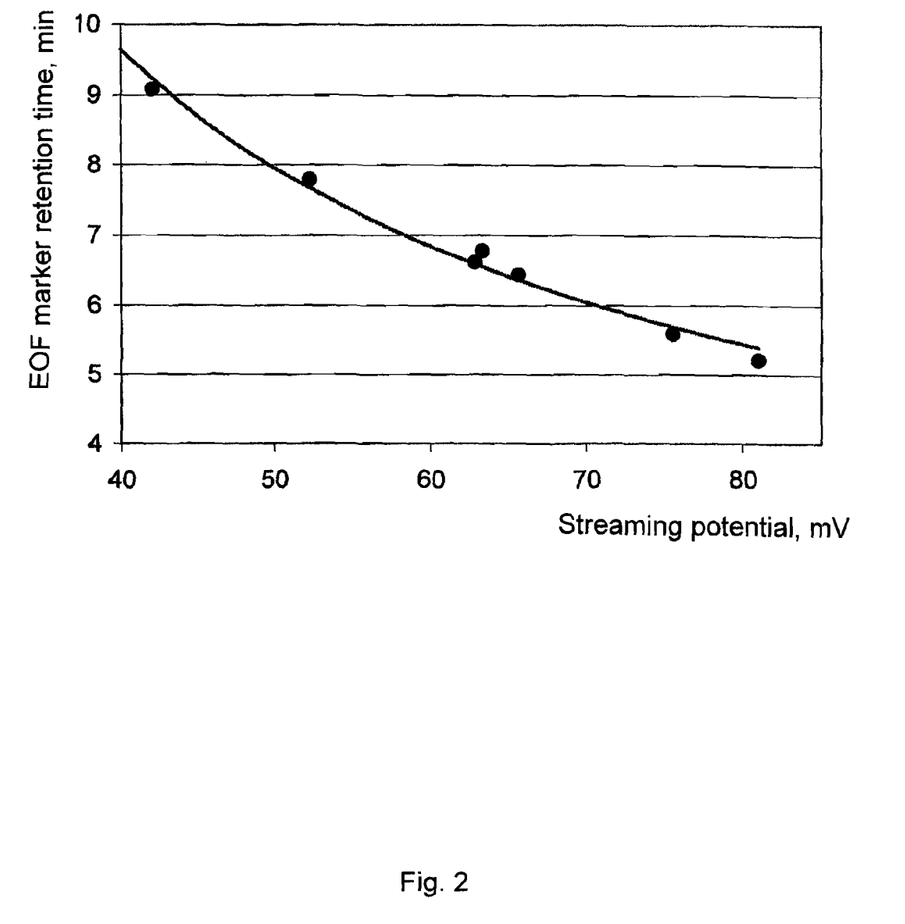
FIG. 2 shows plot of EOF marker retention time against streaming potential magnitude $U_s$.

In both cases the above mentioned unique correspondence is used between electroosmotic flow rate and streaming potential magnitude. FIG. 2 shows the change of electroosmotic flow rate, characterized by retention time of EOF marker at various magnitudes of streaming potential $U_s$. The data obtained in experiment, during which capillary contamination was modeled, introducing a small quantities of cetyl trimethyl ammonium cations into capillary, which absorbed on the surface of capillary and partially disturbed electric double layer structure and reduced the magnitude of streaming potential. It is obvious that experiment confirms availability of unique correspondence between streaming potential magnitude and electroosmotic flow rate value. Thus, the determination of streaming potential magnitude during capillary washing, disclosed in the present invention makes it possible to determine the electroosmotic flow rate value at the successive electrophoretic separation of sample components and to increase reproducibility of electrophoretic analysis of multicomponent solutions.

The disclosed method is applicable in both cases for any type of buffer electrolyte. Both variants are considered below in details.

In the first case, preferable for provision of maximal reproducibility of analysis of multicomponent solutions; for identification of sample components the set values of retention times of known components are used, and at washing equal cleanliness of capillary is obtained both before separation of calibration mixture solutions and before separation of samples, components of which are subject to identification and quantitative analysis. As a criterion of obtaining equal cleanliness of capillary it is used acceptable streaming potential deviation value $dU_s$ from equilibrium value $U_{eq}$, characterizing clean capillary. In this case such threshold value $U_{s0}$, which is less than equilibrum value of streaming potential magnitude $U_{eq}$ by the specified acceptable deviation value $dU_s$, i.e. $U_{s0}=U_{eq}-dU_s$.

Literature or other a priori data may be used to set retention time of known components. In preferred embodiment of the invention the mentioned set values of retention time of known components are determined experimentally at the electrophoretic separation of these known components; before the mentioned separation of calibration mixture washing is made with measurement of streaming potential until obtaining threshold value of streaming potential $U_{s0}$.

In the first case of implementation of the invention the order of value of streaming potential measurement error is chosen to provide high cleanness of capillary and increase reproducibility as acceptable streaming potential deviation value $dU_s$ from equilibrium value $U_{eq}$.

However, at making electrophoretic separation with a few components, retention times of which strongly differs, in the first case of implementation of invention the specified acceptable deviation value $dU_s$ is increased, as a rule, for the purpose of reducing time of washing. For this purpose permissible scatter of sample components retention times is determined, within the limits of which no component identification errors arise while using the set values of retention times of known components, e.g. known components measured at separation of calibration mixture solution. Based on permissible scattering of retention times, the permissible scattering of electroosmotic flow rates is determined. Using dependency between retention time of electroosmotic flow rate marker and streaming potential (FIG. 2), it is determined the acceptable streaming potential deviation value $dU_s$ from equilibrium value, characterizing clean capillary.

In FIG. 1 threshold value of streaming potential, selected according to the first case, is corresponding to the first threshold value $U_{s0\text{-}1}$, obtained at the fifth washing only. At the subsequent washings change of streaming potential is insignificant, therefore the subsequent washings are cancelled. Thus, the first case of implementation of the invention provides significant growth of reproducibility of electrophoretic separation due to the fact that scattering of electroosmotic flow rates does not exceed the acceptable value.

In the second case of implementation of the invention, preferred for its productivity at making large number of analyses of samples of one kind, to identify sample components the measured retention times of components are compared to set retention times of known components using corrections determined by ratio between the measured limit value of streaming potential $U_s$ and the set value of streaming potential $U_{s\text{-}set}$.

The mentioned corrections are determined using dependency between electroosmotic flow rate and streaming potential. The mentioned dependency is determined by calculation method, e.g. using equations (1) and (2), or experimentally, e.g. using EOF markers at different values of streaming potential (FIG. 2) or by means for separation of reference solutions with known components at different magnitudes of streaming potential.

Using of the mentioned corrections compensates influence of scattering of electroosmotic flow rates on retention times of components. Therefore in the second case the electroosmotic flow rate during washings shall reach or exceed minimal permissible value, at which total time of sample separation does not exceed the preset one.

Using dependency of retention time of electroosmotic flow rate marker from streaming potential (FIG. 2), electroosmotic flow rate threshold value $U_{s0}$ is determined by minimal acceptable rate.

As well as in the first case it is preferable to determine the mentioned set values of retention times of known components experimentally in process of electrophoretic separation of these known components; before said separation of calibration mixture washing is made with measurement of streaming potential to obtain threshold value of streaming potential $U_{s0}$, and streaming potential magnitude $U_{s\text{-}cal}$, measured before the end of washing is fixed and used for identification of separated sample components of unknown composition; the invention provides two methods of using this value for calibration. In the first method said set magnitude of streaming potential $U_{s\text{-}set}$, used to determine corrections in process of identification, is taken equal to value $U_{s\text{-}cal}$, measured before separation of calibration mixture, and specified set values of retention times are selected equal to values of retention times of known components, measured during the mentioned separation of calibration mixture. In the second method values of retention times of known components, measured at the electrophoretic separation of these known components $U_{s\text{-}cal}$, determined before electrophoretic separation of calibration mixture of known components with the set streaming potential magnitude $U_{s\text{-}set}$, are selected as the mentioned set values of retention times of known components. The second method of calibration is preferable in the event that separation is required of some calibration solutions of known components, while the magnitudes of streaming potential $U_{s\text{-}cal}$, measured before separation of different calibration mixtures, vary.

As a rule, in the second case of implementation of invention the threshold value is sufficiently lower than in the first case, and consequently, is reached considerably earlier. In FIG. 1 the threshold magnitude of streaming potential, selected according to the second variant, conforms to the second threshold value $U_{s0\text{-}2}$, which is reached at the second washing. Thus, the second case of implementation of invention enables to sufficiently increase efficiency of making large number of analyses of samples of one kind, and sufficiently increases efficiency of electrophoretic separation for the account of using corrections compensating influence of scattering of electroosmotic flow rates on retention times of components.

Figure 3:
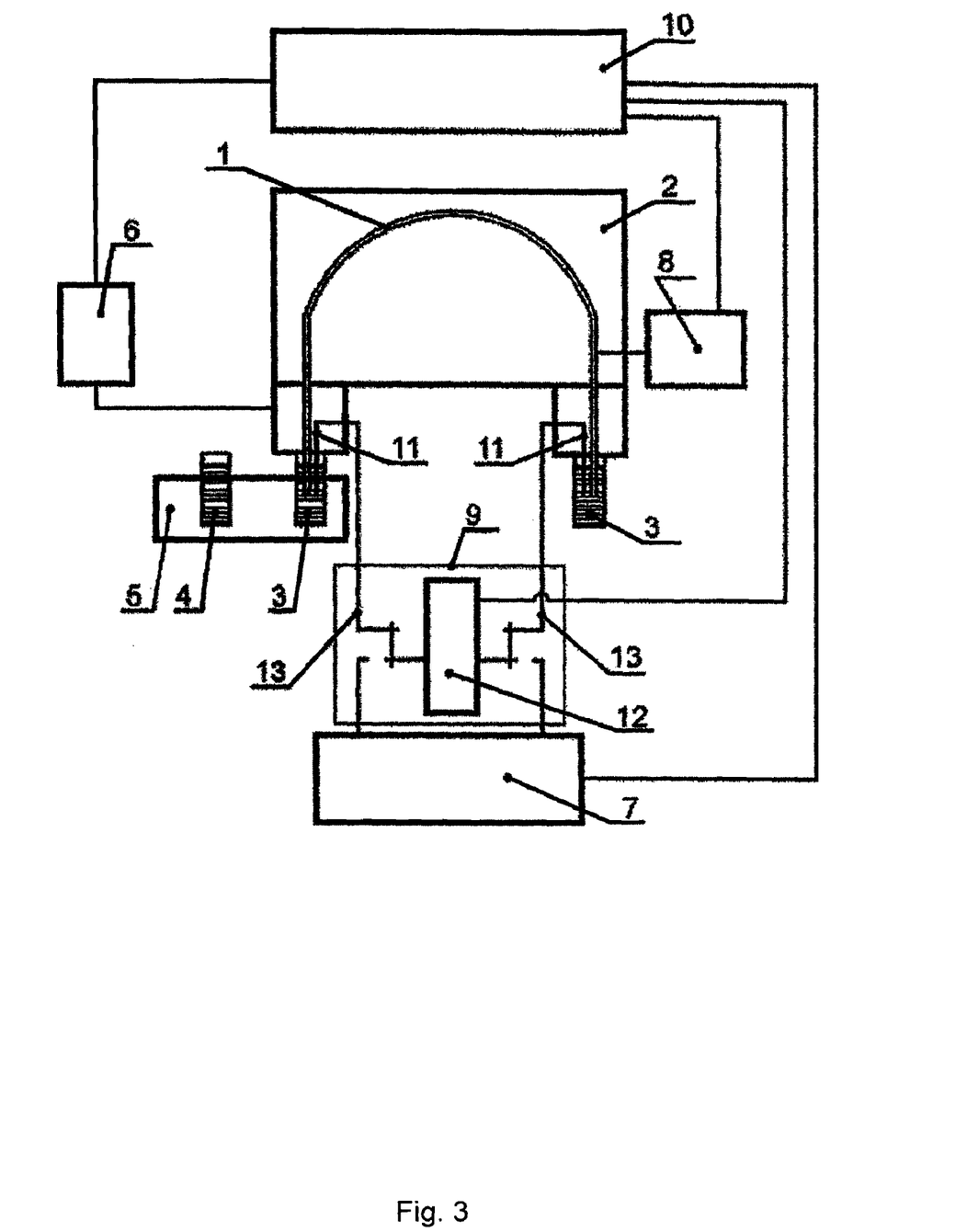
FIG. 3 shows block diagram of the claimed device using high voltage relay for disconnecting of measurement circuit.

FIG. 3 shows block diagram of device of electrophoretic analysis of multicomponent solutions, implementing the method of present invention.

The device contains capillary 1, placed into means for capillary installation 2, vials for electrolyte 3 and 3', vials for sample 4, means for moving said vials 5, made with possibility of immersing capillary ends to said vials.

Figure 4:
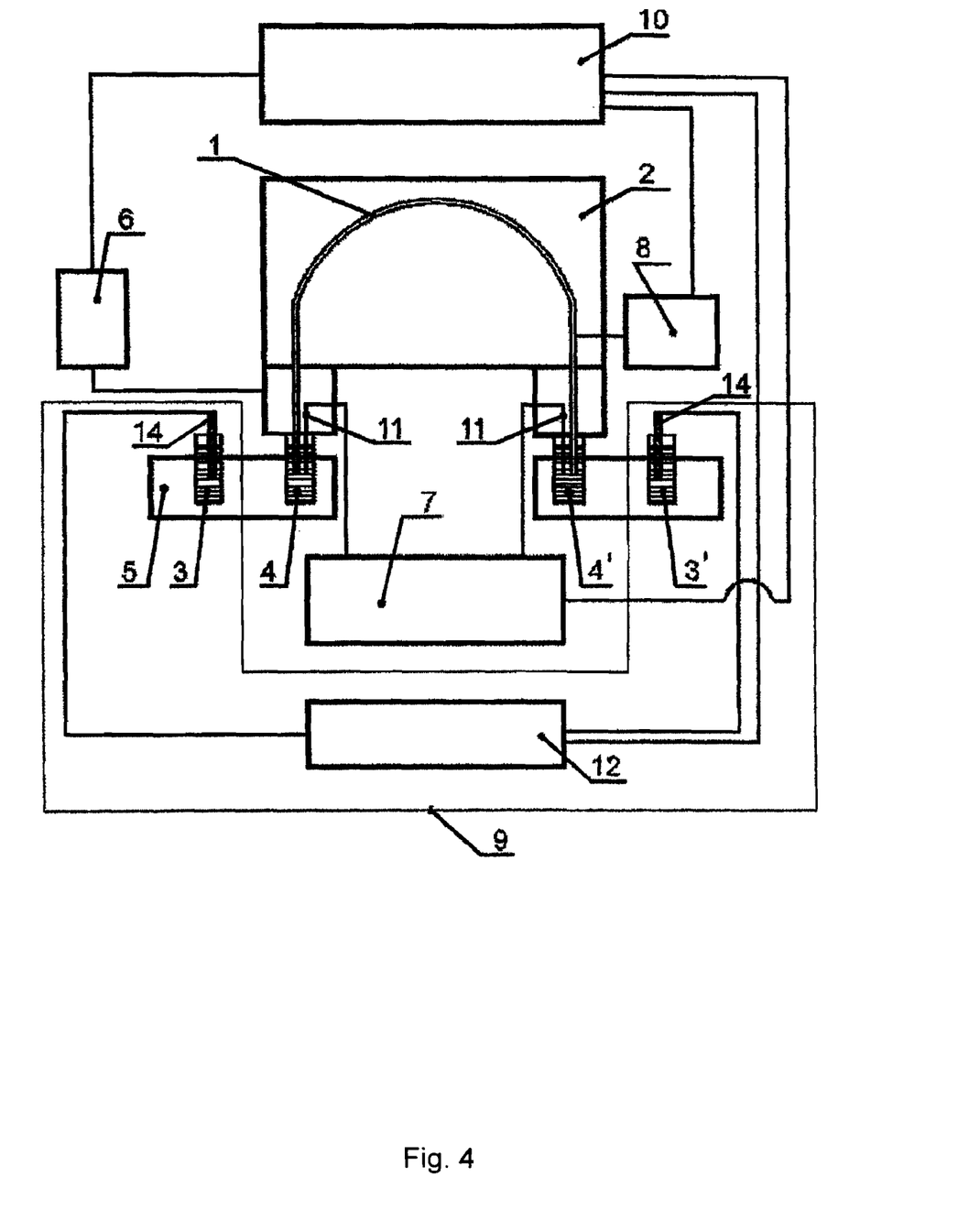
FIG. 4 shows block diagram of the device using measuring electrodes and means for moving vials for disconnecting of measurement circuit.

Means for creation of electrolyte flow through capillary 6 connected with this vial, where the input capillary 1 end was located (in FIGS. 3 and 4 left). Means for applying voltage between ends of capillary 7 are electrically connected with those vials, where ends of capillary 1 were located.

Means for streaming potential measurements 9 were made with possibility of electric connection with ends of capillary 1 during washing. The device contains detector 8, made with possibility of connection with capillary 1. The control and signal processing system 10 is connected with detector 8, means for applying voltage 7, as well as means for creation electrolyte flow through capillary 6 and measurement instrumentation for streaming potential 9.

Instrument of moving vials 5 is a device for moving vials with solutions, and is made by the method known from the prior art, e.g. using electromechanical drive or power drive. Location of selected vial, providing position at the selected capillary end, will be hereinafter referred to as working position of vial.

Capillary 1, as a rule, is made as quartz capillary with protection polymeric coating, that is removed at submersible capillary ends and capillary section, connected with detector 8 in case of using optic detector.

Instruments of installation of capillary 2 are made to provide immersion of capillary 1 ends into vials 3 and 3', being in working position, separation of inner chamber of at least one vial being in working position, from ambient air and connection of the mentioned chamber with instruments of creation electrolyte flow through capillary 6. In the preferred embodiment of the invention construction of instrument of capillary 2 installation provides location of capillary 1 in flushing channel of liquid thermal medium with the set temperature, providing better stabilization of capillary temperature at electrophoretic separation and decreasing scatter of components retention times due to uncontrolled temperature change.

Means for generation of electrolyte flow through capillary 6 is a device for creation and maintenance of set pressure difference between the ends of capillary, submerged to vials with solutions it is implemented by method known from the prior art, for example using compressor and pressure difference sensor with possibility of maintenance of set pressure in the mentioned internal chamber.

Means for applying voltage 7 is a stabilized high voltage source, produced by any known method providing installation of selected high voltage amplitude within the range from zero to maximum. As a rule, maximal amplitude is within the range of 20-40 kilovolt. In the preferred embodiment of the invention the means for applying voltage 7 is made with possibility of switching polarity of high voltage, applied between the ends of a capillary 1.

Means for applying voltage 7 is equipped with electrodes 11, installed so to submerge their ends to vials 3 and 3', being in working position. As electrodes 11, platinum electrodes are used, as a rule.

Means for streaming potential measurement 9 includes an instrument for pressure differential measurement 12 between the ends of capillary, made by method known from the prior art, for example as differential amplifier with large input resistance, sufficiently exceeding electric resistance of capillary filled with electrolyte. As electric resistance of capillary filled with electrolyte, may reach few dozens of MΩ, in the preferred embodiment of the invention the input resistance of amplifier is selected within the range of dozens GΩ. Means for streaming potential measurements 9, electrolyte in vials 3, installed in working position, and capillary 1 filled with electrolyte form an electric measurement circuit.

Means for streaming potential measurements 9 includes also means for opening streaming potential measurements circuit 13 providing prevention of high voltage effect to the mentioned device for potential difference measurement 12.

Means for opening electric measurement circuit 13 may be implemented by any known method, e.g. using high voltage relay, electrically connected at least with one of electrodes 11.

In one aspect of the present invention, preferred according to streaming potential measurement accuracy, alternative way of electric circuit commutation is presented: high voltage, used at electrophoretic separation, and low voltage, measurement, used at washing. Measurement of opening measurement electric circuit includes measurement electrodes 14 (FIG. 4), electrically connected with device of measurement of potential difference 12 measurement instrument of streaming potential 9 and installed in vials filled with buffer electrolyte 3 and 3', which by means for instruments of vials movement 5, is installed in working position at conditioning capillary 1 and measuring streaming potential. Before applying high voltage to electrodes 11, vials 4 and 4' with buffer electrolyte are installed in working position, and vials 3 and 3' with measurement electrodes 14 are taken out of working position, as a result of which measurement electric circuit appeared open. As measurement electrodes 14, electrodes with small residual polarization are used, e.g. chlorine-silver ones, that increases streaming potential measurement accuracy.

As a detector 8 any known detector type for capillary electrophoresis is used, e.g. optical, electrochemical or mass-spectrometric one. One skilled in the art can find, that in case of using mass-spectrometric detector at separation, only input capillary end was put into vial with buffer electrolyte, and instruments of measurement streaming potential are implemented taking into account compatibility with input interface of the mass-spectrometric detector.

The control and signal processing system 10 is implemented by method known from the prior art, e.g. using microprocessor controller and personal computer.

Let us consider in details the example of implementation of the claimed method using the claimed apparatus according to FIG. 3.

To prepare for electrophoretic separation capillary 1 is rinsed with solutions of preliminary washing, selected according to type of substances absorbed earlier, as well as the type of buffer electrolyte used in previous analyses. New capillary or capillary not used for a long time are first washed with acid solution, water, alkali solution, and washed by water again. Then conditioning of capillary is made, i.e. rinsing with the same buffer electrolyte, which will be used in the next analysis.

Washings are made as follows: the selected washing vial with solution of the successive preliminary washing and buffer electrolyte is installed in working position, where the end of capillary 1 is submerged into washing solution of selected vial, and internal chamber of the selected vial is separated from ambient air and pneumatically connected with means for generating electrolyte flow through capillary 6, making excessive pressure, displacing washing solution through capillary 1 to collecting vial (not shown in the figure).

Figure 5:
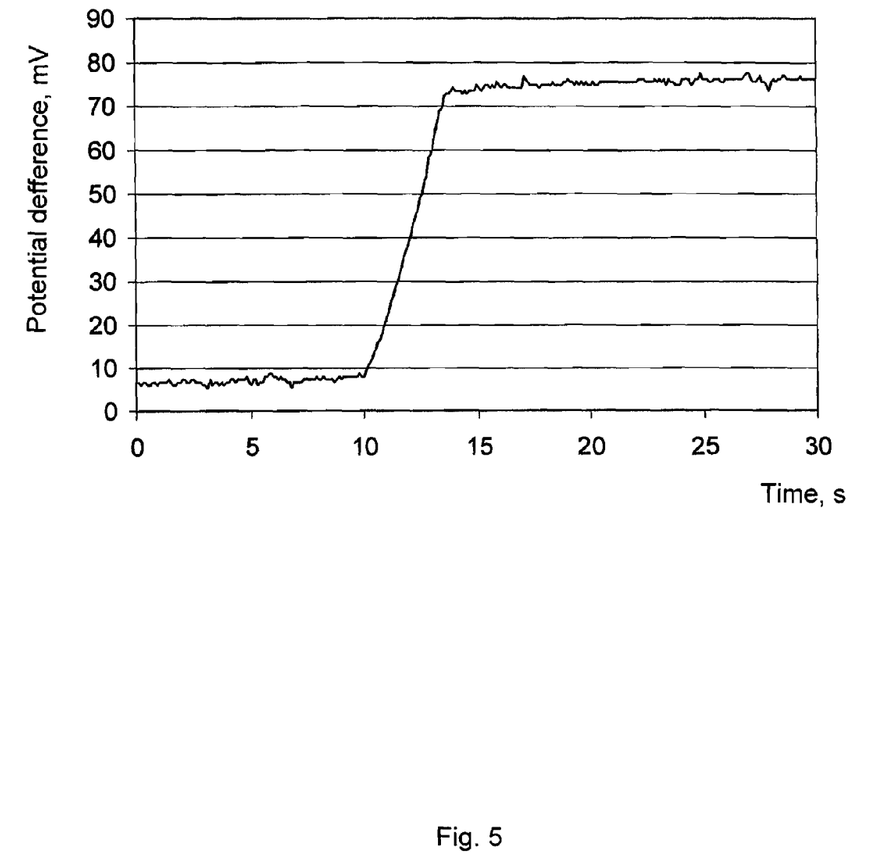
FIG. 5 shows potential difference between capillary ends as a function of time during initial period of washing mode at zero, growing and stabilized pressure between capillary ends.

At the final washing stage in process of capillary conditioning a streaming potential magnitude is determined. For this purpose vials 3 and 3' with buffer electrolyte are installed in working position opposite input and output ends of capillary 1, where capillary ends are immersed. Synchronously with capillary ends electrodes 11 ends also get to vial of buffer electrolyte. Instrument of applying voltage 7 is switched off the electrodes by means for high voltage relay 13, being part of streaming potential measurement means, streaming potential measurement device 9 closing measurement electric circuit, which contains electrodes 11 and buffer electrolyte in both vials and capillary. Flow generation apparatus 6 provides zero flow through capillary by creation of zero pressure difference between the ends of capillary. Thus streaming potential measurement apparatus measures background potential difference between the ends of capillary, which corresponds in FIG. 5 to section 0-10 sec. Then device of flow generation 6 increases pressure difference between the ends of capillary from zero to selected value, providing growth of flow rate of buffer electrolyte through capillary. In FIG. 5 one can see, that growth of pressure difference between the ends of capillary on section 10-13.5 sec is accompanied by proportional growth of potential difference between capillary ends. After obtaining the selected value of pressure difference the flow generation device 6 maintains the mentioned selected pressure difference between capillary ends and provides the selected flow rate of buffer electrolyte through capillary. Maintenance of permanent flow rate in FIG. 5 corresponds to section 13.5-30 sec. It is obvious that steady flow rate corresponds to a steady (working) potential difference between the capillary ends. Thus, potential difference measurement device measures the magnitude of working potential difference between the ends of capillary, maintaining the selected pressure difference between them. The control and signal processing system 10 receives the measured data and calculates streaming potential, subtracting magnitude of background potential difference from the magnitude of working potential difference.

Figure 6:
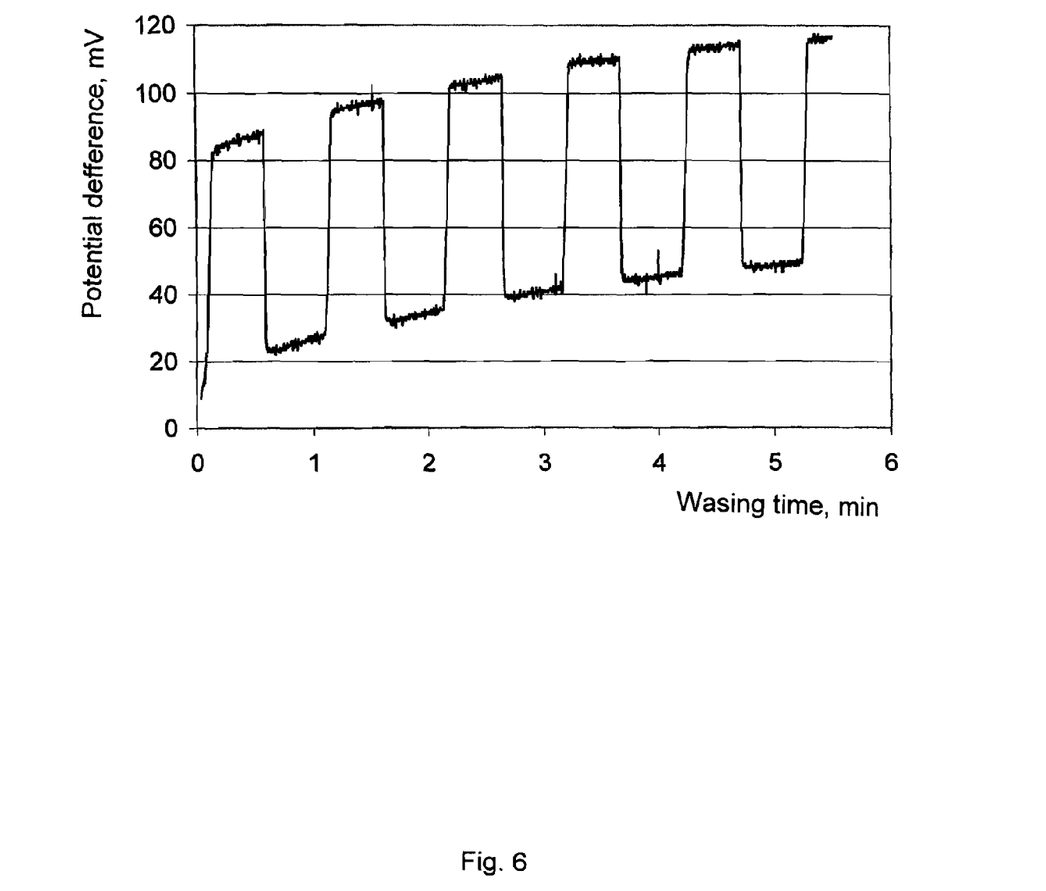
FIG. 6 shows potential difference between capillary ends as a function of time in successive washings of clean capillary.

FIG. 6 shows variation in time of potential difference magnitudes between the ends of clean capillary at alternate presence and absence of pressure difference between its ends. Sections of low value meanders correspond to background potential difference, and sections of higher potential difference magnitudes correspond to working potential difference. It is obvious that both background and working potential difference are changed in time because of measurement system drift, while streaming potential magnitude is constant. That's why in preferred embodiment of the invention series of successive washings is made to increase streaming potential measurement accuracy; at next washing after the set period of time after its beginning potential difference between capillary ends is reduced up to zero and background potential difference is measured again. The background potential difference change measured that way is used for correction of calculated magnitude of streaming potential, which fact sufficiently reduces errors connected with the mentioned drift.

When streaming potential $U_s$ measured and corrected this way is equal or more than preliminary set threshold value $U_{s0}$, procedure of washing is stopped. If $U_s$ is less than the set threshold value $U_{s0}$, a new washing is started, as a result of which new magnitudes of background and working potential differences will be measured, as well as new obtained magnitude $U_s$ will be determined. All the procedure is made until $U_s$ reaches or exceeds the preset threshold value $U_{s0}$.

After the completion of capillary washing a dozing injection of selected sample is made into capillary. For this purpose the vial 4 with selected sample is installed into working position, corresponding to input end of capillary 1 by device moving vials 5. As a sample one may select either solution of calibration mixture of known components, or solution of unknown composition, components of which are subject to identification and qualitative analysis. Injection of sample is made by any known method including, for example, electrokinetic one. In the preferred embodiment of the invention a sample is injected by flow generation apparatus through capillary 6, making the selected pressure difference between ends of capillary 1 during the selected period of time. After injecting sample the vial with buffer electrolyte 3 is installed into working position instead of vial with sample 4, electrodes 11 are disconnected from measurement circuit and connected to high voltage circuit. Then procedure of electrophoretic separation is made, applying to electrodes 11 selected voltage from the means for voltage generation 7 and sending signals from detector 8 to the control and signal processing system 10.

As a result of applying high voltage to capillary ends the components of injected sample begin to move in capillary at different rate. 1 By virtue of the fact that the value of detector 8 signal depends on volume of component in sample, while the next moving component of sample connected with detector 8 passes capillary 1 detection area, the value of detector 8 signal is changed. The control and signal processing system 10 registers detector 8 signal changing in time and calculates retention time of each detected sample component equal to time interval between the beginning of electrophoretic separation and the moment of this component detection.

Retention times measured for different sample components are used for their identification, comparing them to the set retention times of known components, while measured signal amplitudes of detector are used to calculate the concentration of identified components in sample.

Literature or other data, obtained for other device, may be used as set retention time of known components. In preferred embodiment of the invention the mentioned set values of retention times of known components are determined at the electrophoretic separation of calibration mixture of these known components, made by the method mentioned above with the same device used for electrophoretic sample separation.

In the first case mentioned above of implementation of the invention; for identification of sample components the measured retention times of components are compared to set retention times of known components. Thus, the significant growth of reproducibility of electrophoretic separation is due to the fact that scattering of electroosmotic flow rates does not exceed the acceptable value in different analyses.

In the second case of implementation of the invention, for identification of sample components the measured retention times of components are compared to set retention times of known components using corrections determined by method mentioned above from the ratio between the measured magnitude of streaming potential and the set magnitude of streaming potential. Thus, the efficiency of making large number of analyses of samples of one kind sufficiently increases, and reproducibility of electrophoretic analysis of sample composition increases sufficiently by means of using corrections compensating influence of scattering of electroosmotic flow rates on retention times of components.

As example of separation and analysis of multicomponent mixture components results of analysis of model mixture is shown below, consisting of benzil alcohol, N-phenyl lithium anthranilate and lithium benzoate in 0.001 M solution of sodium tetraborate. The prepared solution was used for calibration of experimental model of CE system with streaming potential measurement unit. Calibration was made using a data collection and processing software and recorded as analysis method. All further analyses were made according to the same analysis method using the recorded calibration. Retention times for components, averaged over three parallel measurements, and their concentrations (according to production procedure) are shown in table 1.

TABLE 1

Averaged parameters of calibration electropherograms.

| Benzil alcohol | | N-phenyl lithium anthranilate | | Lithium benzoate | |
| --- | --- | --- | --- | --- | --- |
| Time, min | Concentration, mg/dm³ | Time, min | Concentration, mg/dm³ | Time, min | Concentration, mg/dm³ |
| Result 3.879 | 400.00 | 5.641 | 50.00 | 6.474 | 100.00 |

The measured magnitude of streaming potential was 82.5±0.2 mV in average before calibration measurements.

To simulate capillary contamination that can not be controlled by operator, similar to that taking place after analyses of samples with different composition of mixtures, cetyl trimethyl ammonium bromide was injected into capillary before washing, so that to obtain concentration of 0.001 mole/dm$^3$, and after that the capillary was washed for different time intervals, inherently insufficient for complete cleaning of capillary inner surface. That is, sample injected after washing was analyzed in conditions of various efficiency of capillary cleanliness. In successive analyses series the following retention times and concentrations of determined components were obtained:

TABLE 2

Results of electrophoretic sample analysis after "uncontrolled" capillary contamination.

|  | Benzil alcohol | | N-phenyl lithium anthranilate | | Lithium benzoate | |
| --- | --- | --- | --- | --- | --- | --- |
|  | Time, min | Concentration, mg/dm$^3$ | Time, min | Concentration, мг/дм$^3$ | Time, min | Concentration, mg/dm$^3$ |
| No. 1__dirt | 4.733 | 312.86 | 7.579 | 51.03 | 9.187 | 111.26 |
| No. 2__dirt | 4.251 | 262.59 | 6.488 | 40.54 | 7.641 | 84.47 |
| No. 3__dirt | 4.23 | 264.29 | 6.449 | 38.48 | 7.598 | 81.12 |
| No. 4__dirt | 4.223 | 296.79 | 6.455 | 43.34 | 7.606 | 90.90 |
| No. 5__dirt | 4.174 | 301.53 | 6.341 | 44.96 | 7.448 | 93.22 |
| No. 6__dirt | 4.186 | 298.18 | 6.375 | 45.00 | 7.505 | 93.91 |
| No. 7__dirt | 4.084 | 388.66 | 5.96 | 55.35 | 6.946 | 106.67 |
| av. value | 4.27 | 303.56 | 6.52 | 45.53 | 7.70 | 94.51 |
| Abs. RMS error | 0.21 | 42.09 | 0.50 | 5.87 | 0.70 | 10.98 |
| deviat. from calibr. | 10.0% | −24.1% | 15.6% | −8.9% | 19.0% | −5.5% |
| Rel. RMS error | 5.0% | 13.9% | 7.7% | 12.9% | 9.0% | 11.6% |

Typical magnitudes of streaming potential magnitude before analytic measurements were from 67 mV (for experiment No.6) to 80 mV (for 7th experiment).

The last two lines of the table show how much measurement results of table2 deviated from values for calibrated measurements of table1 (deviation from calibration), as well as the scatter of measurement results in this series of seven successive analysis (Rel. RMS error=root-mean-square deviation of results from an average value).

It is obvious that deviation from calibration values for peak retention time is from 10 to 19 percent for all three analyzed substances, and from 5.5 to 24 percent for calculated concentration. The reproducibility of measurement (Rel. RMS error) is also rather low: from 5 to 9 percent for retention time, and from 8 to 14 percent for calculated concentration.

To demonstrate the effect of reproducibility increase for peak retention time and growth of accuracy of determination of concentrations caused by use of streaming potential magnitude at washing the following experiment was executed. After each injection of contaminating solution of cetyl trimethyl ammonium bromide, capillary was washed with solution of basic electrolyte (0.01 M solution of borax): first the basic washing within three minutes without streaming potential measurement, and then additional washing, alternating with stages of streaming potential measurement. Periodicity of additional washing was selected equal 1 minute: 30 seconds of washing and 30 seconds of streaming potential measurement. Limit magnitude of streaming potential, at which capillary was considered ready for the following sample injection, was selected equal to 82 mV. Capillary washing was automatically stopped when the mentioned value was reached (as a rule, after the 3$^{rd}$-4$^{th}$ additional washing). Then analysis of model solution was made. The received data is presented in table 3.

TABLE 3

Example of reproducibility of retention times of components and analysis of concentrations using capillary washing till obtaining the set magnitude of streaming potential.

|  | Benzil alcohol | | N-phenyl lithium anthranilate | | Lithium benzoate | |
| --- | --- | --- | --- | --- | --- | --- |
|  | Time, min | Concentration, mg/dm$^3$ | Time, min | Concentration, mg/dm$^3$ | Time, min | Concentration, mg/dm$^3$ |
| No. 1__clean | 3.862 | 405.93 | 5.625 | 49.90 | 6.466 | 100.97 |
| No. 2__clean | 3.85 | 387.95 | 5.621 | 50.12 | 6.464 | 101.80 |
| No. 3__clean | 3.866 | 368.88 | 5.647 | 51.26 | 6.505 | 105.21 |
| No. 4__clean | 3.907 | 408.79 | 5.755 | 50.13 | 6.645 | 101.26 |
| No. 5__clean | 3.923 | 407.31 | 5.789 | 51.25 | 6.69 | 104.47 |
| No. 6__clean | 3.935 | 394.27 | 5.817 | 51.15 | 6.735 | 105.96 |
| av. value | 3.89 | 395.52 | 5.71 | 50.64 | 6.58 | 103.28 |
| Abs. RMS error | 0.04 | 15.44 | 0.09 | 0.65 | 0.12 | 2.19 |

TABLE 3-continued

Example of reproducibility of retention times of components and analysis of concentrations using capillary washing till obtaining the set magnitude of streaming potential.

| | Benzil alcohol | | N-phenyl lithium anthranilate | | Lithium benzoate | |
|---|---|---|---|---|---|---|
| | Time, min | Concentration, mg/dm³ | Time, min | Concentration, mg/dm³ | Time, min | Concentration, mg/dm³ |
| Deviat. from calibr. | 0.3% | −1.1% | 1.2% | 1.3% | 1.7% | 3.3% |
| Rel. RMS error | 0.9% | 3.9% | 1.5% | 1.3% | 1.8% | 2.1% |

Based on the last lines of tables 2 and 3, related to deviation of measurement results from calibration ones and reproducibility parameters for these series of measurements, table 4 was made, showing improvement of parameters of deviation from calculation values and parameter of reproducibility of results (both for retention times and calculated values of concentration).

TABLE 4

Effect of washing of capillary to obtaining the magnitude of streaming potential set magnitude (based on data of tables 2 and 3).

| | Benzil alcohol | | N-phenyl lithium anthranilate | | Lithium benzoate | |
|---|---|---|---|---|---|---|
| | in respect to time | in respect to concentration | in respect to time | in respect to concentration | in respect to time | in respect to concentration |
| Deviat. from calculat. | 33.9 | 21.5 | 12.9 | 7.0 | 11.2 | 1.7 |
| Rel. RMS error | 5.4 | 3.6 | 5.0 | 10.1 | 4.9 | 5.5 |

Table 4 shows that for electrophoretic analysis of multicomponent samples using streaming potential measurement a sufficient improvement is observed of both reproducibility of retention times and accuracy of concentration analysis. Thus, improvement of reproducibility of retention times for three substances of model solution (Rel. RMS error in time) is from 4.9 to 5.4, and improvement of reproducibility of analysis of concentration of components (Rel. RMS error for concentration) is from 5.5 to 10. Thus accuracy of determination of mean values of retention times and concentrations relative to values for calibration solutions improved even more sufficiently: from 11 to 34 percent for retention times, and from 1.7 to 21.5 percent for concentrations.

One skilled in the art can find that detailed description is made above as an example, and many other variants may be proposed, within the limits of this invention, including, e.g. the variants not described here in details: variant of measurement streaming potential just after electrophoretic separation with determination of appropriate corrections or variant of generation of electrolyte flow through capillary by means for negative pressure difference on output end of capillary, as well as variant of modification of implementation of method in apparatus while using mass-spectrometric detector, but not limited to these examples.

LITERATURE

1. R. Weinberger. Practical Capillary Electrophoresis. 2 Edit., Academic Press, 2000.

2. Dale R. Baker. Capillary Electrophoresis. John Wiley & sons, Inc., 1995.

3. Capillary Electrophoresis Manual. Edited by A. M. Voloshchuk, M., 1996

4. Capillary Electrophoresis System. Bases of the method. Equipment. Examples of capillary electrophoresis system use "Kapel-103,-104,-105". SPb, "Petropolis" Publishing House 2001.

5. U.S. Pat. No. 5,441,613 (also known as WO-A1 No.1996022151).

What is claimed is:

1. A device for electrophoretic analysis of multicomponent solutions comprising a capillary having capillary ends, a plurality of vials for electrolyte and sample solutions, a means for setting up said capillary ends and said vials implemented to immerse said capillary ends into said vials, a means for generation of electrolyte flow, a means for applying voltage across said capillary ends, a detector connected to said capillary, and a controlling and signal processing system, wherein the device further comprises a streaming potential measurement means implemented to measure a potential difference between said capillary ends and to form an electric connections with said capillary ends during capillary rinsing in such a way that said streaming potential measurement means and electrolyte inside said capillary and said vials form a closed measurement electric circuit, and said means for generation of electrolyte flow is implemented so as to build up and maintain a preset differential pressure between said capillary ends, and wherein said streaming potential measurement means comprises a means to disconnect said measurement electric circuit during electrophoretic analysis.

2. A device according to claim 1, wherein said means for setting up capillary ends and vials is implemented to pneumatically connect an internal cavity of the vial containing a solution in which one of capillary ends is immersed, with a means for generation of electrolyte flow, said means for generation of electrolyte flow is implemented so as to maintain a preset pressure within said internal cavity of the vial.

3. A device according to claim 1, wherein said means to disconnect measurement electric circuit comprises first and second vials for electrolyte solution implemented so as to immerse a capillary end into said first vial during streaming potential measurements and into said second vial during electrophoretic separation, said first vial contains measurement electrode.

4. A device according to claim 1, wherein said electric connections between said capillary ends immersed in electrolyte solution and both said means for applying voltage across capillary ends and said streaming potential measurement means are achieved by using two common electrodes that are sequentially incorporated in said means for applying voltage across capillary ends or said streaming potential measurement means.

5. A device according to claim 4, wherein said two common electrodes are switched into said streaming potential measurement means while said electrodes are disconnected from said means for applying voltage across capillary ends by said means to disconnect measurement electric circuit during capillary rinsing electrophoretic analysis.

6. A device according to claim 5, wherein said two common electrodes are switched into said means for applying voltage across capillary ends while said electrodes are disconnected from said streaming potential measurement means by said means to disconnect measurement electric circuit during electrophoretic analysis.

7. A device according to claim 1, wherein the means to disconnect said measurement electric circuit comprises a means for disconnecting said measurement electric circuit.

* * * * *